(12) United States Patent
Staples, II et al.

(10) Patent No.: US 11,935,630 B2
(45) Date of Patent: Mar. 19, 2024

(54) SYSTEM ASSISTED DATA BLENDING (71) Applicant: CERNER INNOVATION, INC., Kansas, KS (US)

(72) Inventors: Alan Harris Staples, II, Shawnee, KS (US); Karen Kaye Ramsey, Lenexa, KS (US); Jason Sachan, Overland Park, KS (US)

(73) Assignee: Cerner Innovation, Inc., Kansas City, KS (US)

(*) Notice: Subject to any disclaimer, the term of this patent is extended or adjusted under 35 U.S.C. 154(b) by 523 days.

(21) Appl. No.: 14/584,689

(22) Filed: Dec. 29, 2014

(65) Prior Publication Data
US 2016/0188843 A1    Jun. 30, 2016

(51) Int. Cl.
*G16H 10/20*    (2018.01)
*G06F 16/335*    (2019.01)
*G16H 10/60*    (2018.01)
*G16Z 99/00*    (2019.01)

(52) U.S. Cl.
CPC ........... *G16H 10/20* (2018.01); *G06F 16/335* (2019.01); *G16H 10/60* (2018.01); *G16Z 99/00* (2019.02)

(58) Field of Classification Search
CPC ...... G16H 10/20; G16H 10/60; G06F 16/335; G16Z 99/00
See application file for complete search history.

(56) References Cited

U.S. PATENT DOCUMENTS

| | | | |
|---|---|---|---|
| 8,111,626 B2* | 2/2012 | Shaikh | H04L 41/0631 370/242 |
| 2002/0147867 A1 | 10/2002 | Satlow | |
| 2004/0204957 A1 | 10/2004 | Afeyan et al. | |
| 2007/0033070 A1 | 2/2007 | Beck et al. | |
| 2007/0094253 A1* | 4/2007 | Bent | G06F 17/30539 |
| 2008/0201280 A1* | 8/2008 | Martin | G06N 99/005 706/12 |
| 2011/0099140 A1* | 4/2011 | Ridgeway | G06F 19/345 706/50 |
| 2012/0036523 A1* | 2/2012 | Weintraub | H04N 7/173 725/9 |

OTHER PUBLICATIONS

Non-Final Office Action dated Feb. 16, 2018 in U.S. Appl. No. 14/680,263, 23 pages.

(Continued)

*Primary Examiner* — Eliza A Lam
(74) *Attorney, Agent, or Firm* — Mughal Gaudry & Franklin PC (57) ABSTRACT

Methods, systems, and computer-readable media are provided for blending data. The system may identify user behavior patterns such that relevant correlations are learned by the system and suggested to a user automatically. The system may also analyze each available data set to identify both present and potential correlations to suggest to a user. This provides an efficient means for the system to automatically narrow a compilation of data sets into a filtered group of suggested data sets for a user. Put another way, the system gathers data on user behavior and known correlations and uses various methodologies to generate new data sets to be automatically compared and catalogued.

20 Claims, 5 Drawing Sheets

(56) References Cited

OTHER PUBLICATIONS

Non-Final Office Action received for U.S. Appl. No. 14/680,263, dated May 9, 2017, 19 pages.

Pending U.S. Patent Application by inventor Bruce Howard Kusens, U.S. Appl. No. 14/058,439, filed Oct. 21, 2013, entitled "Method And Process For Obtaining Consent To Access And Populate A Personal Health Record".

Pending U.S. Patent Application by inventor Bruce Howard Kusens, U.S. Appl. No. 14/099,532, filed Dec. 6, 2013, titled "Preventive Care Engine".

Pending U.S. Patent Application by inventor Bruce Howard Kusens, U.S. Appl. No. 13/671,437, filed Nov. 7, 2012, titled "Electronic Identification Of Healthcare Claims Where Third-Party Liability May Exist".

Pending U.S. Patent Application by inventor Bruce Howard Kusens, U.S. Appl. No. 13/691,772, filed Dec. 1, 2012, titled "Method For Verification Of Prescription Medication Compliance".

Pending U.S. Patent Application by inventor Bruce Howard Kusens, U.S. Appl. No. 14/058,658, filed Oct. 21, 2013, titled "Method Of Identifying Patient Healthcare Comorbidities From Electronic Healthcare Records".

Pending U.S. Patent Application by same inventor Bruce Howard Kusens, U.S. Appl. No. 14/984,921, filed Dec. 30, 2015, titled "Healthcare Assurance System".

Pending U.S. Patent Application by inventor Bruce Howard Kusens, U.S. Appl. No. 14/074,845, filed Nov. 8, 2013, titled "Method To Obtain And Manage Patient Medical Record Disclosure Consents".

Pending U.S. Patent Application by inventor Bruce Howard Kusens, U.S. Appl. No. 15/179,415, filed Jun. 10, 2016, titled "Method And System For Determining Third Party Liability Utilizing Single Or Multiple Data Sources".

Pending U.S. Patent Application by inventor Bruce Howard Kusens, U.S. Appl. No. 14/671,916, filed Mar. 27, 2015, titled "Method To Deliver And Collect Patient Data Based Upon Healthcare Provider Location And Permissions".

Pending U.S. Patent Application by inventor Bruce Howard Kusens, U.S. Appl. No. 14/680,263, filed Apr. 7, 2015, titled "The Electronic Determination Of Healthcare Claims Where Insurance Deductibles Have Not Been Satisfied And/Or The Probability Of Patient Payment Is Low".

Pending U.S. Patent Application by inventor Bruce Howard Kusens, U.S. Appl. No. 15/186,392, filed Jun. 17, 2016, titled "Method And System To Obtain And Manage Medical Records".

\* cited by examiner

SYSTEM ASSISTED DATA BLENDING

BACKGROUND

Healthcare includes many complex and highly integrated workflows. Determining factors that directly impact the workflows can be challenging. The ability to understand what those factors are is crucial to maximizing performance and adjusting processes to address true causative factors rather than addressing things that only seem to have a correlation.

Additionally, individuals managing these complex decisions often do not have significant experience with statistical analysis. Because of this, they may not know how to correlate data points or be able to determine if the results of their analysis are truly relevant or not. Furthermore, when selecting data sets to evaluate, without any preliminary suggestions, a user is simply guessing from an infinite number of combinations.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for data blending. In particular, this disclosure describes system assisted ad hoc data blending. A system that assists users by ensuring the data is managed appropriately as it is analyzed is described. The system may provide validity to user selected correlations by scoring correlation coefficients between selected data points. The system may also suggest relevant data sets to investigate and indicate which data sets are not relevant based on standards of statistical analysis. The system may utilize data available in one or more patients' electronic medical records (EMR).

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for data blending. In particular, this disclosure describes system assisted ad hoc data blending. User-selected data sets may be validated by a system that scores correlation coefficients of the data points within the user-selected data sets. Relevant data sets, determined by the system using statistical analysis, may be suggested to a user. Data sets may also be suggested to a user based on user behavior patterns learned by the system. Additionally, data sets that are selected and not relevant or not selected and not relevant may be indicated to a user. Data from EMR's may be utilized to provide the above-recited information as well as artificial intelligence techniques (e.g., machine learning, etc.) and any other data relevant to the statistical analysis including statistical standards.

A first aspect is directed to a computerized method, carried out by at least one server having one or more processors. The method includes, in part, receiving an indication of a first data set; automatically evaluating a plurality of data sets to identify one or more data sets of the plurality of data sets that includes a correlation with the first data set; and providing the one or more data sets having a correlation with the first data set with an indication that the one or more data sets having a correlation with the first data set has been identified to include said correlation.

A second aspect is directed to a system for data blending. The system includes one or more processors; and one or more computer storage media storing computer-useable instructions that, when used by the one or more processors, cause the one or more processors to: automatically evaluate a plurality of data sets to identify one or more data sets of the plurality of data sets that includes a correlation with a first data set; and provide the one or more data sets having a correlation with the first data set along with an indication that the one or more data sets having a correlation with the first data set has been identified to include said correlation.

A third aspect is directed to one or more computer-readable media having computer-executable instructions embodied thereon that, when executed, facilitate a method of data blending. The method includes receiving an indication of a first data set; identifying a plurality of data sets available to blend with the first data set; identifying, within the plurality of data sets available to blend with the first data set, one or more data sets to recommend to a first user for blending with the first data set based on user behavior patterns of the first user; and providing to the first user both the one or more data sets to recommend based on the user behavior patterns of the first user and at least one data set having a correlation with the first data.

Figure 1:
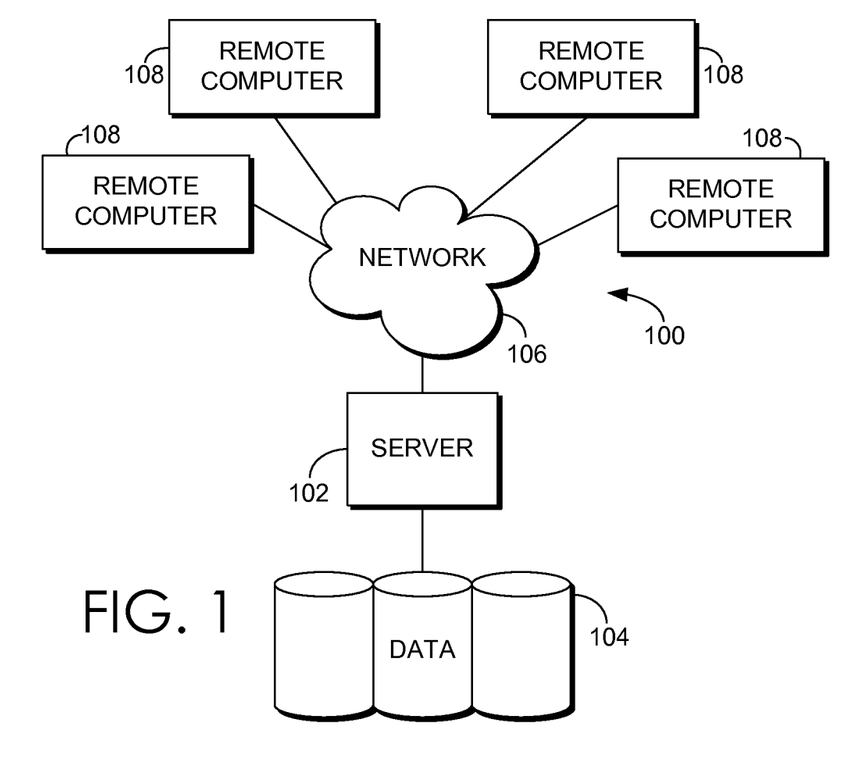
FIG. 1 is a block diagram of an exemplary computing system suitable to implement embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like. Additionally, the present invention may be operational in any setting managing large amounts of data, not only a medical setting.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer-readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health-care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

In some embodiments, the computing system 100 is a multi-agent computing system with one or more agents. But it will be appreciated that the computing system 100 may also take the form of a single agent of a non-agent system. The computing system 100 may be a distributed computing system, a centralized computing system, a single computer such as a desktop or laptop computer or a networked computing system.

In some embodiments of the invention, the computer system 100 is a multi-agent computer system with agents. The multi-agent system may be used to address issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy.

Embodiments using a multi-agent system provide capabilities to adapt the frequency and messages used for communication between the system 100 and one or more users, based on changes to the environment and provide capabilities to filter out noisy data, thereby providing more flexible and adaptable decision making abilities. In some embodiments, this is accomplished by using leveraging preceptors and effectors. Preceptors or sensors, which in some embodiments may be agents, detect changes in an operating environment and pass this information to the agent system. Effectors, which in some embodiments may be agents, respond directly to changes in an operating environment and consider goals and alternatives prior to implementing a change to the environment.

Embodiments using multi-agent systems further have the capability of supporting intelligent information retrieval and filter out noisy data and utilize heuristics to narrow down a search space to assist in solving complex problems. The multi-agent system facilitates designing individual agent behaviors and their interactions with other agents and users. In some embodiments, agents encoded with both declarative and procedural knowledge can therefore learn by means of exploration of knowledge and imitation of other agents, for example, by leveraging aggregation of bottom-up and top-down modeling. In some embodiments, the agent system accepts an abstract workflow and converts it into an actual executable workflow, by for example, using contract and negotiation in multi-agent systems. The executable workflow may then leverage agents to run the actual workflow.

Embodiments using multi-agent systems coordinate the actions of the agents to cooperate to achieve common objectives, and negotiate to resolve conflicts, which allows for adaptability, flexibility, and organizational relationships. The transformation of heterogeneous knowledge and content into homogeneous knowledge and content is an important trait of the multi-agent system to provide interoperability. The multi-agent system operates to achieve its goals while still interacting with agents, including agents outside of the multi-agent system and users at a higher degree of flexibility.

Figure 2:
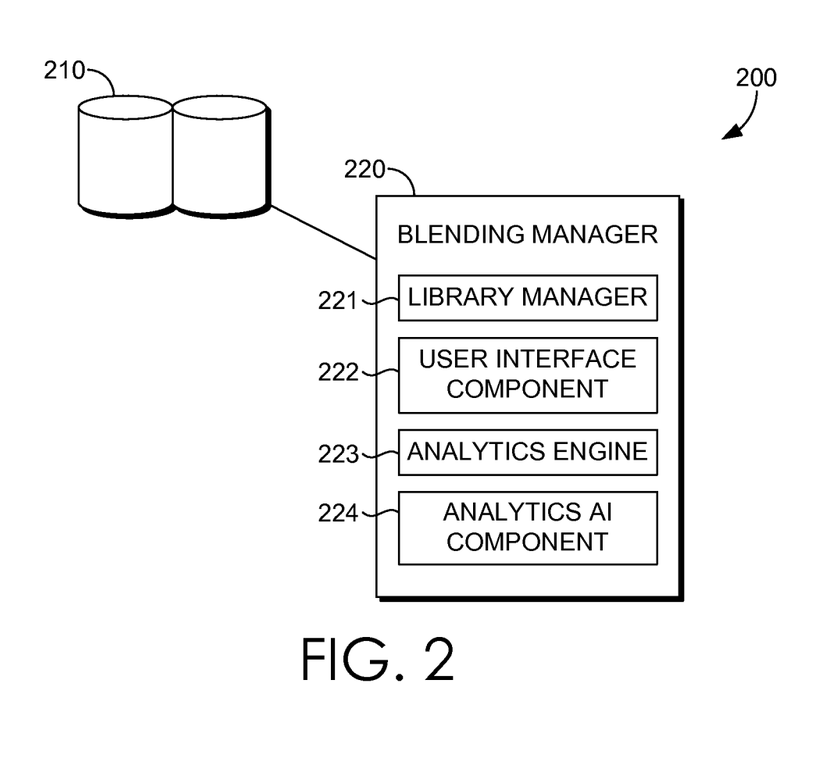
FIG. 2 depicts an exemplary computing system suitable to implement embodiments of the present invention.

Turning now to FIG. 2, exemplary system architecture 200 suitable for implementing embodiments of the present invention is illustrated. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown (including a network and a user device, among others), the system 200 may include a database 210 and a blending manager 220. The database 210, while illustrated as a single database for simplicity, may in reality be a plurality of databases associated with the same or different sources. Examples of sources can include data from traditional hospitals, walk-in clinics, urgent care facilities, and other locations that render medical services. Data can also be retrieved from centralized data sources such as health information exchanges. Data from any other source can also be included. For example, a database may be an EMR database for Institution A while a second database may be an EMR database for Institution B, a branch office of Institution A. Additional data stores include big data and small data and, as such, may be embodied as cloud data stores. Furthermore, external public and private data stores (e.g., weather data, census data) may be accessed via web services or similar means. In embodiments, the database 210 includes one or more data sets available to blend. A data set, as used herein, refers generally to a compilation of data points. For example, an exemplary data set may be a data set of on-time starts for a particular surgeon (i.e., data on when the surgeon started on time and when the surgeon did not start on time). An additional exemplary data set may be a weather data set including weather patterns for a location. As such, the data set is represented as the mechanism to retrieve it from the raw data, i.e., a query. Data sets may be pulled directly from a patient's EMR or a plurality of EMRs.

In embodiments, the database 210 is a collection of databases including cloud data stores and local data stores (e.g., data stores associated with a specific source). In each data store, a library of queries is maintained. Only raw queries, devoid of demographics, location, or time information, exist in the data stores. The database 210 may also include filters that are tracked. Filters, as used herein, refer generally to limitations on queries. For instance, a specific date range may be applied to a query, a particular clinician, a location, a time of day, etc. Relationships between data sets may depend on filters so it is important that filters are tracked.

The database may be in communication with the blending manager 220 or components thereof and may include rules for the blending manager 220. The rules for the blending manager 220 may include a set of rules or library of rules. In one embodiment, rules are useable by an expert rules-engine, such as an agent in a multi-agent system.

The blending manager 220 may be configured to perform blending management for the system 200. The blending manager 220 may include a library manager 221, a user interface component 222, an analytics engine 223, and an analytics AI (artificial intelligence) component 224. Each component of the blending manager 220 may be an agent in a multi-agent system rather than components of the blending manager 220. Each component (or agent, in an embodiment) provides enhanced decision support by using multi-agent properties like collaboration, persistence, mobility and distributed-operation, autonomy, adaptability, knowledge and intelligence, reactive and proactive capability, reuse, scalability, reliability, maintainability, security, fault tolerance, trust, and other primary properties. In addition, numerous secondary properties of multi-agents in embodiments of the invention may facilitate decision support including: reasoning, planning and learning capabilities; decentralization; conflict resolution; distributed problem solving; divide-and-conquer strategies for handling complex problems; location transparency; allowing for competing objects to be represented; goal-driven or data driven including agent to agent or user to agent; time driven; support for multiple layers of abstractive above services thereby providing flexibility, adaptability, and reuse and simplification; negotiation; hierarchies having dynamic self-organization; abilities to spawn and destroy agents as needed; utilization of transient and persistent data; abilities to address uncertain, missing, or inconsistent data; sensitivity to resource and time constraints; ontology-driven functionality; flexible run-time invocation and planning; obligations; ability to act to achieve objectives on behalf of individuals and organizations; organizations influence; and other secondary properties. Examples of agents, which may be used by the multi-agent system herein include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: markov decision processing; approximate linear programming; natural language extraction solvers (e.g., nCode); fuzzy-neural networks, logistic and linear regression; forward chaining inference (e.g., data driven); backward chaining inference (e.g., goal driven); inductive inference; genetic algorithm; neural network including genetic algorithm for training; stochastic; self-organizing Kohenen map; Q-learning; quasi-Newton; gradient; decision trees; lower/higher bound search; constrain satisfaction; naives bayes fuzzy; LP-solver including mixed integer multi-variable min/man solvers; Finite State Machine and HFSM; temporal difference reasoning; data mining for classification, clustering, learning and prediction; K-means; support vector machines; K-nearest neighbor classification; C5.0; apriori; EM, simulated annealing, Tabu search, multi-criteria decision making, evolutionary algorithm, and other similar solvers.

Some embodiments of the invention employ decision making for applications including, for example, searching, logical inference, pattern matching and decomposition. Decision making solvers may be used. Decision making solvers are a special set of solvers used for decision making, although it is contemplated that in some embodiments any solver or solver agent may be used for decision processing. Examples of agent decision processing applications include: searching, including heuristic and traditional searching; list; constraint satisfaction; heuristic informed; hill climbing; decision tree; simulated annealing; graph search; A* search; genetic algorithm; evolutionary algorithm; tabu search; logical inference; fuzzy logic; forward and backward chaining rules; multi-criteria decision making; procedural; inductive inference; pattern recognition; neural fuzzy network; speech recognition; natural language processing; decomposition; divide and conquer; goal tree and sub-goal tree; state machine; function decomposition; pattern decomposition; and other decision processing applications. In some embodiments, agents designed or instantiated with a particular decision processing application may be swapped out, in a more seamless and transparent manner than with non-agent systems, with another agent having more advanced decision processing functionality as is available or is needed.

Returning to FIG. 2, the library manager 221, while illustrated for simplicity as a component of the blending manager 220, may be a separate component in direct communication with the database 210. In embodiments, the library manager 221 is an intermediate component between the database 210 and any other component of the blending manager 220. The library manager 221 may be configured to, among other things, track and report statistics on unique entities. A unique entity, as used herein, refers generally to a combination of a query and one or more filters. Each combination is a unique entity. Tracked statistics may include average run time per degree of X, average data size per degree of X, known concurrencies to other unique entities (e.g., a data set is known to have a correlation with another data set), etc. The library manager 221 is also configured to manage system tracking such that it does not run too long, exceeding a predetermined period of time.

The user interface component 222 may be configured to, among other things, provide a means for users to easily peruse queries or data sets. The user interface component 222 may provide one or more filters for a user to apply. An exemplary user interface 300 is provided in FIG. 3. The user interface 300 illustrates a date range filter at date range input area 304. The user interface component 222 also provides a data set area 306 that includes one or more data sets as illustrated by data set 312A and data set 312B. One or more data sets may be selected from the data set area 306 and moved (or dragged) to the data set display area 312 for analysis. As an example, data set 312A and data set 312B have been selected in FIG. 3 and dragged to the data set display area 312 such that graphical representation 312A displays data set 312A, graphical representation 312B displays data set 312B, and graphical representation 312C displays an overlap of data set 312A and data set 312B.

Figure 3:
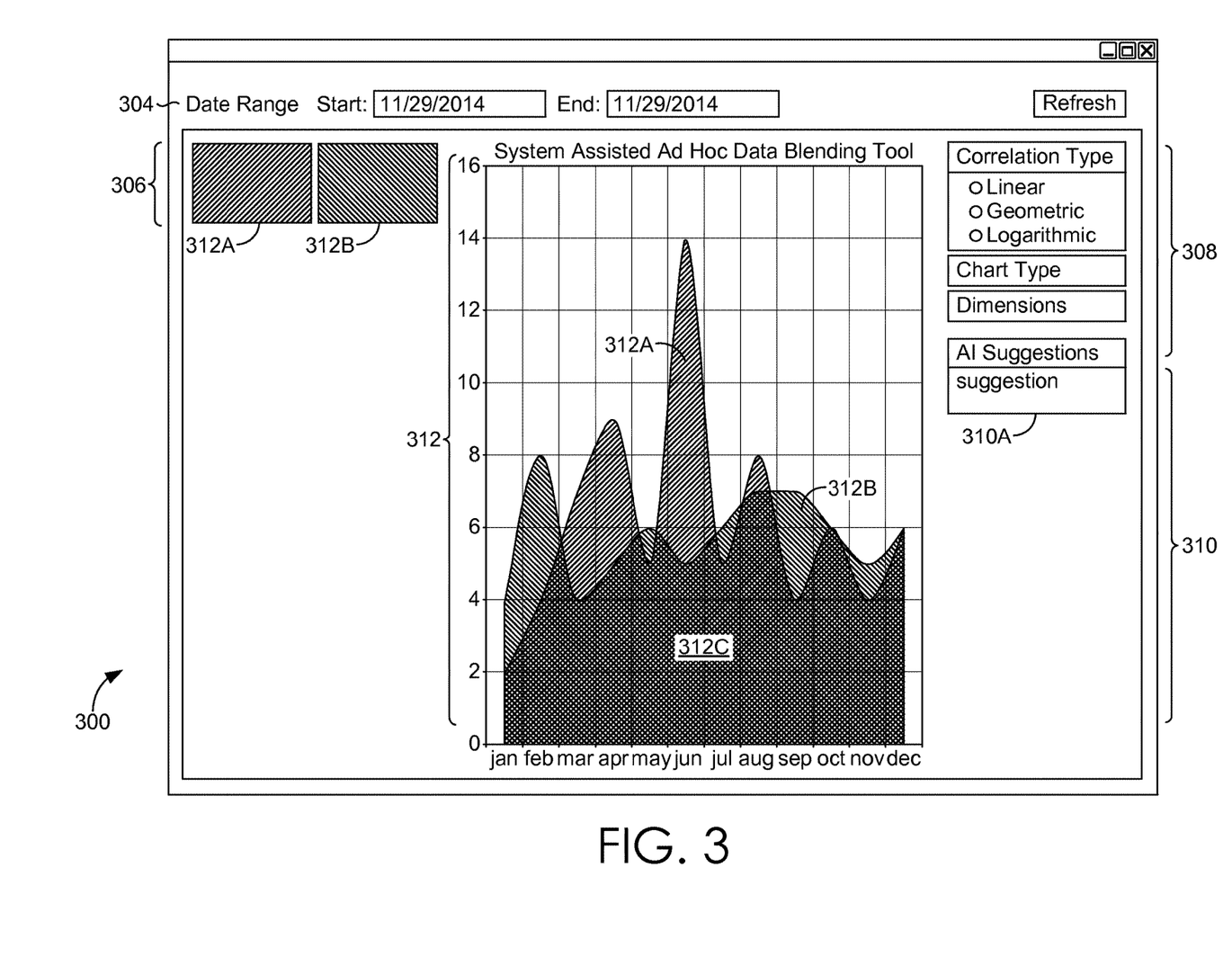
FIG. 3 depicts an exemplary graphical user interface (GUI) illustrating a data blending dashboard, in accordance with an embodiment of the present invention.

The user interface component 222 may also provide a display options area 308 where a user may adjust the correlation type, chart type (e.g., bar graph, etc.), or dimensions of the data set display area 312. The user interface 222 may also provide an AI suggestion area 310. As illustrated in FIG. 3, the AI suggestion area 310 includes a suggestion 310A. The suggestion may be one or more data sets suggested to analyze, a suggested filter to apply to a data set, and the like. Potential suggestions will be discussed in further detail below.

Returning now to FIG. 2, the analytics engine 223 may be configured to, among other things, gather (e.g., receive, retrieve, etc.) lists of unique entities and perform concurrency checks on them. The lists may be externally supplied lists. The analytics engine 223 may make findings available for consumption by external sources.

The analytics AI component 224 may be configured to, among other things, monitor usage of the user interface. Through monitoring, the analytics AI component 224 may determine what queries/data sets/entities are commonly used. Commonly used, as used herein, refers generally to a data set that is used more than a predetermined number of times. This may be user-specific. Alternatively, this may be a most commonly used data set (ranked 1-100, for example) used by a particular user. The analytics AI component 224 may also learn what queries/data sets/entities have correlations/concurrencies, which are found to most often be a part of a concurrency, which are least used. Least used, as used herein, refers generally to a data set that is used less than a predetermined number of times. Alternatively, 'least used' may be identified from a data set ranking (1-100, for example) indicating common and least used data sets. From the information learned, the analytics AI component 224 may suggest both potential and novel matches of its own, which may be communicated to the analytics engine 223 for a random sampling of tests and then to the user interface component 222 for display.

As previously described, various independent agents can make up the analytics AI component 224 in system 200. For example, this may be a multi-agent system with one or more agents, a single agent system, or a non-agent system. Each agent may leverage a particular strategy to uncover previously undiscovered relationships in the data. Each agent's strengths may be leveraged in an AI component, while its weaknesses may be mitigated by other agents. The strategies may include, among others, machine learning, expert system, neural network, big data, and the like. Machine learning may be used to map out predefined subsets of blending jobs and provide full coverage of those via scheduled jobs. New relationships could be found in those batched jobs. Expert system may be used to target unstructured or semantic data, where different terms may be used for the same meaning. Neural network, a self-organizing system, may be used to learn to recognize similar patterns in both the data and in human interaction with the user interface and to make blending suggestions to users. Big data may be an intermediary to a global data store where known relationships discovered by other installations are warehoused. These can be suggested to a user as new blending ideas. Over time, results from one agent may be used to update other agents. For example, the machine learning module may have its predefined subsets updated to include new relationships based on information coming in from the Big Data module.

The analytics AI component 224 may be utilized to further narrow down data sets into a manageable number of data sets. By way of example, the analytics AI component 224 may analyze 50,000 data sets to identify correlations. The analytics AI component 224 may do this using any strategy described herein (e.g., machine learning, neural network) and, using the one or more strategies, identify correlations that may be present among the data sets. The data sets may be narrowed (or filtered) using user behavior patterns. User behavior may be used to identify data sets that are frequently used (i.e., used greater than a predetermined number of times), infrequently used (i.e., used less than a predetermined number of times), frequently used in combination with a selected data set, infrequently or never used in combination with the selected data set, previously viewed data sets (i.e., a data set previously viewed by a user at a time prior to the present), etc. Frequency may also be defined as a ranking associated with a data set as defined by a user or assigned to a data set based on use by the user.

The user behavior patterns may be user specific such that each user has a unique behavior pattern that is learned by the analytics AI component 224. The user behavior patterns may also be per-group for each group created by an administrator. A group may include two or more users. The analytics AI component 224 may also learn the decision of the user to evaluate whether a suggestion was actually relevant or not. For instance, if Data Set Y was suggested to the user but determined to not be relevant to the user, the analytics AI component 224 may indicate the identified correlation that caused the suggestion in the first place to not actually be relevant so that in the future, under the same conditions, Data Set Y is not suggested again. User behavior patterns may be continuously monitored. Furthermore, in an embodiment, analytics AI component 224 may discard data sets that are found to not be relevant (e.g., by a user under a specific filter), to not have a correlation under any conditions, or are not associated with a user behavior patterns specific to a current user.

In any environment utilized, there may be an infinite number of data sets that can be extracted from the raw data. The system 200 provides an intelligent, autonomous system that will take cues from users, and its own learning, to effectively and efficiently generate magnitudes more data sets than a human can possible generate and to automate the comparison process. During an initial setup, any known data sets may be input into the system. The system may then catalog the results of its efforts including each data set it generates, how it was generated, which other data sets is was compared to, and what correlations were found.

Unique entities (e.g., combinations of queries and filters) then generate specific data sets. As a correlation may only exist between two specific data sets, the unique entities are a useful way to describe how to find the data that contains the correlation. For example, 'First Case On Time Starts' is a query. Unfiltered, it is a huge data set representing all cases a facility has seen since initiation of the system. A multitude of statistically significant correlations can exist within that one measure when appropriately filtered (e.g., by a given surgeon, date range, operating room, average overtime hours, policy enforcement, procedure type, patient health, etc.). The system is intended to enhance a user's ability to select meaningful data sets and automate the comparison process.

By way of example, assume that an Operating Room (OR) Director wants to understand why the percentage of on-time starts for the first cases of the day was lower than expected last month. The OR director believes this may be related to several days of bad weather that occurred and caused issues with staff and patients arriving on time. In the tool, such as user interface 300, the OR director can pull the on-time start data and the recent weather data. Each of the on-time start data and the weather data may be displayed, for example, in the data set area 306. The OR director would, for instance, simply select the desired data set (such as weather data) and drag it to the data set display area 312. The system 200 performs an analysis of the two data sets and their potential correlation. The system 200 is also simultaneously suggesting a potential correlation between on-time start percentages and the documented surgeons if the sample size were larger. The suggestions may be presented, for example, in the AI suggestion area 310 of FIG. 3. The system 200 may also suggest a present correlation that that OR director may want to evaluate. The OR director may select any suggestion (of the AI suggestion area 310) and "drag" it to the data set display area 312 for analysis.

Present and potential correlations may be distinguished using visual identifiers or any other identifier capable of distinguishing items (e.g., color codes, icons, etc.). Identifiers used to indicate a correlation type (e.g., present or potential) may be referred to as status indicators. Status indicators may also include information related to or indicating a statistically relevant correlation of two or more data sets (e.g., correlation coefficient of X or higher), correlation coefficient of type X, where X is, for example, Pearson's, rank, distance, etc., correlation with a larger or smaller sample size (i.e., adjustment is needed), canonical correlations (multiple data points with related indicator), or no statistically relevant correlation.

A present correlation refers to an actual, existing correlation identified by the system with a selected data set under current filters. For example, the OR director may have selected the last 30 days as a time range. A present correlation would have a correlation with a selected data set under the present filter (i.e., 30 day time range). A potential correlation refers to a correlation that does not exist presently or under the present filters but may exist if an adjustment is made to one or more filters. For instance, if the time range were expanded to 45 days or shortened to 15 days a potential correlation may be indicated. The system may indicate the adjustment needed along with the suggested potential correlation. Alternatively, the adjustment may be displayed by way of an adjustment indicator (e.g., any visual indicator designated to identify an adjustment is needed).

The system also provides the user the ability to view multiple available data sets and drag them onto a graphical display to display the data appropriately (e.g., in a line chart with appropriate scale). Adding additional measures would automatically adjust the scale of the graphic to match levels of granularity across the data sets without altering integrity of the data.

As another example, assume that a user would like to identify a reason for an increase in the number of procedures cancelled on the day the procedure is scheduled to occur. Upon selecting the data set representing the number of procedures cancelled the day they were scheduled, the system automatically evaluates the remaining data sets. The system may identify present or potential correlations in one or more data sets and suggest those data sets to the user. For instance, the user may identify that a certain surgeon assigned to the cancelled procedures has a higher number of cases with increased complexity than other surgeons. Alternatively, the system may identify that the pre-op department is failing to complete necessary pre-op procedures so the entire procedure is cancelled. Each suggested data set may be associated with one or more indicators indicating a present or potential correlation, whether an adjustment is needed, what adjustment is needed, and the like. An adjustment may also be an indication to combine two or more data sets. For instance, evaluating case on-time starts may not correlate to procedure type alone but when combined with room turn-over time a correlation does exist. Faster turn-over time may allow more time for setting up for complicated procedures, thereby keeping them on-time when they otherwise frequently are not. This is merely one example of a combination of data sets.

The system may also be configured to provide alerts to users in preconfigured situations. For instance, an alert may be generated for a previously viewed data set. Additionally, alerts may be generated for data sets that were previously viewed but under different constraints/filters. An alert may be configured for any desirable situation.

Figure 4:
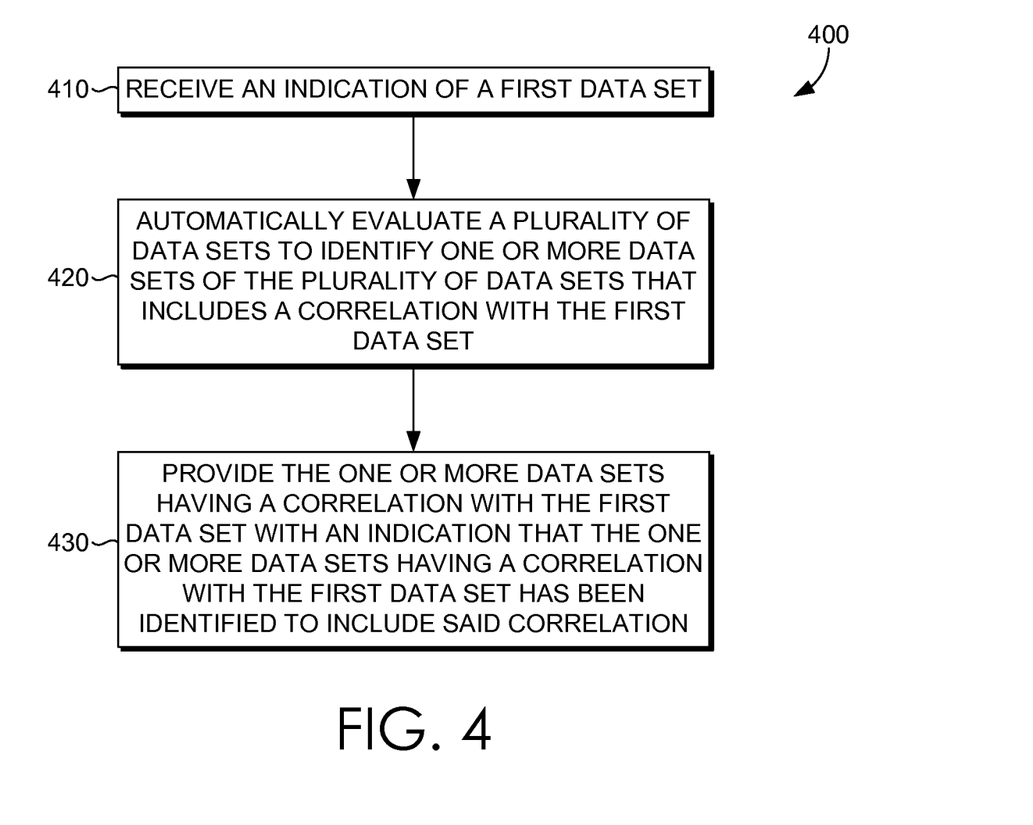
FIG. 4 depicts a flow diagram of an exemplary method for carrying out embodiments of the present invention.

FIG. 4 depicts a flow diagram of a method 400 for blending data, in accordance with an embodiment of the present invention. At block 410, an indication of a first data set is received. At block 420, the system automatically, upon receiving the indication of the first data set, evaluates a plurality of data sets to identify one or more data sets of the plurality of data sets that includes a correlation with the first data set. The analysis to identify correlations between data sets may be performed continuously and the findings catalogued. For instance, when a user first selects a data set, the catalog may be referenced for known correlations.

At block 430, the one or more data sets having a correlation with the first data set is provided with an indication that the one or more data sets having a correlation with the first data set has been identified to include said correlation.

Figure 5:
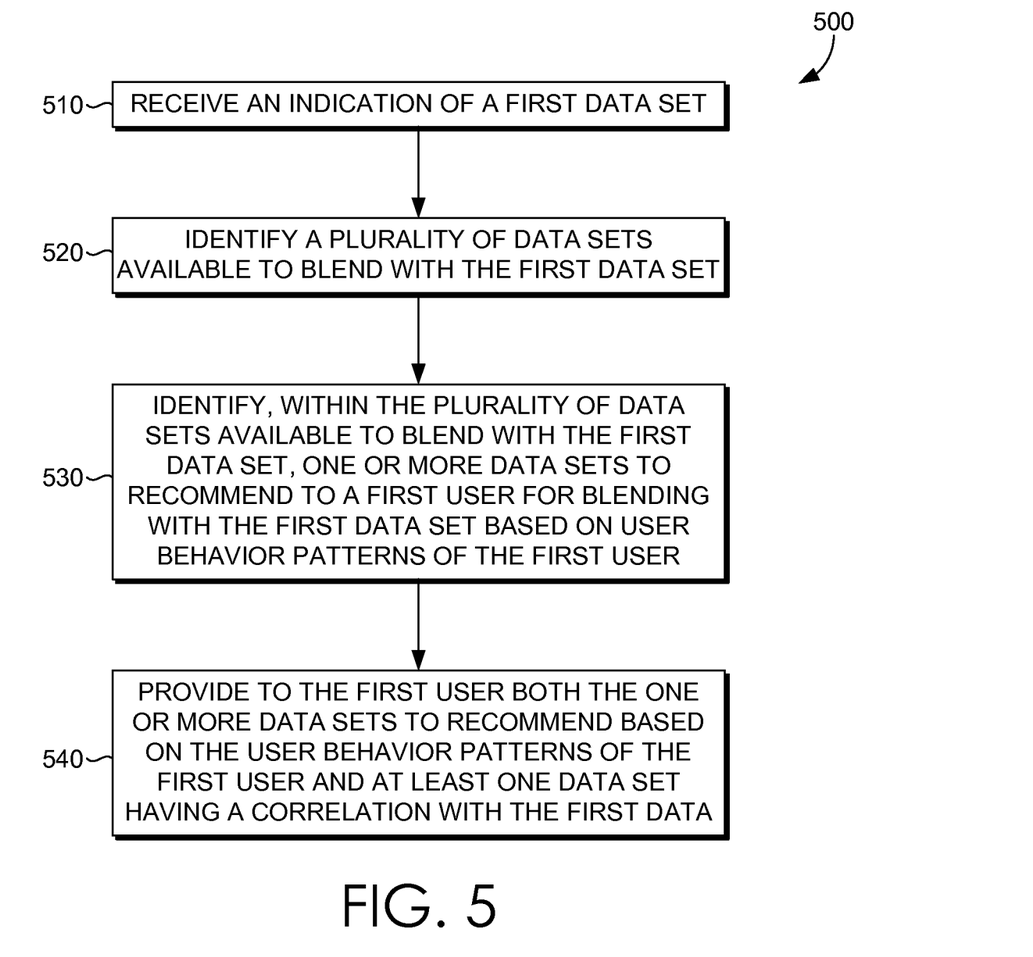
FIG. 5 depicts a flow diagram of an exemplary method for carrying out embodiments of the present invention.

FIG. 5 depicts a flow diagram of a method 500 for blending data, in accordance with an embodiment of the present invention. At block 510, an indication of a first data set is received. At block 520, a plurality of data sets available to blend with the first data set is identified. At block 530, one or more data sets to recommend to a first user for blending with the first data set is identified, from within the plurality of data sets available to blend with the first data set, based on user behavior patterns of the first user. At block 540, both the one or more data sets to recommend based on the user behavior patterns of the first user and at least one data set having a correlation with the first data set are provided to the first user.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more computer storage media having computer-executable instructions embodied thereon that, when executed, facilitate a method of data blending, the method comprising:

receiving an indication of a first data set from a first user; identifying a plurality of data sets available to blend with the first data set; identifying, within the plurality of data sets available to blend with the first data set, a first one or more data sets to recommend to the first user for blending with the first data set based on user behavior patterns of the first user, wherein the first one or more data sets to recommend are identified using a plurality of agents, the plurality of agents employing strategies comprising one or more of machine learning, expert system, neural network, and big data, to determine a first correlation that the first one or more data sets of the plurality of data sets have with the first data set and identify the first one or more data sets of the plurality of data sets that have the first correlation with the first data set, and filtering the plurality of data sets identified by the plurality of agents based on the user behavior patterns of the first user, wherein filtering the plurality of data sets is placing limitations on queries of the plurality of data sets, wherein a result from a first agent of the plurality of agents is used to update a second agent of the plurality of agents;

identifying, within the plurality of data sets available to blend with the first data set, one or more adjustments that when made to a second one or more data sets of the plurality of data sets causes a potential correlation with the first data set and determining the potential correlation that the one or more adjustments to the second one or more data sets of the plurality of data sets will cause the second one or more data sets of the plurality of data sets to have with the first data set;

cataloging and storing the first one or more data sets of the plurality of data sets and the determined first correlation that the first one or more data sets of the plurality of data sets have with the first data set;

displaying to the first user at a graphical user interface, both the first one or more data sets to recommend based on the user behavior patterns of the first user and at least one data set having the first correlation with the first data; and displaying at the graphical user interface, the one or more adjustments, the second one or more data sets of the plurality of data sets, and the potential correlation, wherein the potential correlation becomes a second correlation upon receiving an indication that the one or more adjustments are made.

2. The media of claim 1, wherein the computer-executable instructions, when executed, further cause discarding a third one or more data sets of the plurality of data sets available that either have no correlation with the first data set or are not associated with the first user based on the user behavior patterns of the first user.

3. The media of claim 1, wherein the computer-executable instructions, when executed, further cause continuously monitoring user behavior patterns.

4. The media of claim 1, wherein the one or more adjustments includes adjusting a sample size.

5. The media of claim 1, wherein the one or more adjustments includes combining two or more data sets.

6. The media of claim 1, wherein the computer-executable instructions, when executed, further cause displaying a status indicator that indicates a correlation coefficient of a type including one of a ranking or a distance.

7. The media of claim 1, wherein the user behavior patterns indicate
a frequently used data set, wherein a frequently used data set is used more than a predetermined number of times.

8. The media of claim 1, wherein the user behavior patterns indicate an infrequently used data set, wherein an infrequently used data set is used less than a predetermined number of times.

9. A computerized method of data blending, carried out by at least one server having one or more processors, the method comprising:
receiving an indication of a first data set from a first user;
identifying a plurality of data sets available to blend with the first data set; identifying, within the plurality of data sets available to blend with the first data set, a first one or more data sets to recommend to the first user for blending with the first data set based on user behavior patterns of the first user, wherein the first one or more data sets to recommend are identified using a plurality of agents, the plurality of agents employing strategies comprising one or more of machine learning, expert system, neural network, and big data, to determine a first correlation that the first one or more data sets of the plurality of data sets have with the first data set and identify the first one or more data sets of the plurality of data sets that have the first correlation with the first data set, and filtering the plurality of data sets identified by the plurality of agents based on the user behavior patterns of the first user, wherein filtering the plurality of data sets is placing limitations on queries of the plurality of data sets, wherein a result from a first agent of the plurality of agents is used to update a second agent of the plurality of agents;

identifying, within the plurality of data sets available to blend with the first data set, one or more adjustments that when made to a second one or more data sets of the plurality of data sets causes a potential correlation with the first data set and determining the potential correlation that the one or more adjustments to the second one or more data sets of the plurality of data sets will cause the second one or more data sets of the plurality of data sets to have with the first data set;

cataloging and storing the first one or more data sets of the plurality of data sets and the determined first correlation that the first one or more data sets of the plurality of data sets have with the first data set;

displaying to the first user at a graphical user interface, both the first one or more data sets to recommend based on the user behavior patterns of the first user and at least one data set having the first correlation with the first data; and displaying at the graphical user interface, the one or more adjustments, the second one or more data sets of the plurality of data sets, and the potential correlation, wherein the potential correlation becomes a second correlation upon receiving an indication that the one or more adjustments are made.

10. The method of claim 9, wherein the one or more adjustments includes adjusting a sample size.

11. The method of claim 9, wherein the one or more adjustments includes combining two or more data sets.

12. The method of claim 9, further comprising displaying a status indicator that indicates a correlation coefficient of a type including one of a ranking or a distance.

13. The method of claim 9, wherein the user behavior patterns indicate a frequently used data set, wherein a frequently used data set is used more than a predetermined number of times.

14. The method of claim 9, wherein the user behavior patterns indicate an infrequently used data set, wherein an infrequently used data set is used less than a predetermined number of times.

15. A system for data blending, the system comprising:
one or more processors; and
one or more computer storage media storing computer-useable instructions that, when used by the one or more processors, cause the one or more processors to:
receive an indication of a first data set from a first user;
identify a plurality of data sets available to blend with the first data set; identify, within the plurality of data sets available to blend with the first data set, a first one or more data sets to recommend to the first user for blending with the first data set based on user behavior patterns of the first user, wherein the first one or more data sets to recommend are identified using a plurality of agents, the plurality of agents employing strategies comprising one or more of machine learning, expert system, neural network, and big data, to determine a first correlation that the first one or more data sets of the plurality of data sets have with the first data set and identify the first one or more data sets of the plurality of data sets that have the first correlation with the first data set, and filter the plurality of data sets identified by the plurality of agents based on the user behavior patterns of the first user, wherein filtering the plurality of data sets is placing limitations on queries of the plurality of data sets, wherein a result from a first agent of the plurality of agents is used to update a second agent of the plurality of agents;

identify, within the plurality of data sets available to blend with the first data set, one or more adjustments that when made to a second one or more data sets of the plurality of data sets causes a potential correlation with the first data set and determine the potential correlation that the one or more adjustments to the second one or more data sets of the plurality of data sets will cause the second one or more data sets of the plurality of data sets to have with the first data set;

catalogue and store the first one or more data sets of the plurality of data sets and the determined first correlation that the first one or more data sets of the plurality of data sets have with the first data set;

display to the first user at a graphical user interface, both the first one or more data sets to recommend based on the user behavior patterns of the first user and at least one data set having the first correlation with the first data; and display at the graphical user interface, the one or more adjustments, the second one or more data sets of the plurality of data sets, and the potential correlation, wherein the potential correlation becomes a second correlation upon receiving an indication that the one or more adjustments are made.

16. The system of claim 15, wherein the one or more adjustments includes adjusting a sample size.

17. The system of claim 15, wherein the one or more adjustments includes combining two or more data sets.

18. The system of claim 15, wherein the computer-executable instructions, when executed, further cause displaying a status indicator that indicates a correlation coefficient of a type including one of a ranking or a distance.

19. The system of claim 15, wherein the user behavior patterns indicate
a frequently used data set, wherein a frequently used data set is used more than a predetermined number of times.

20. The system of claim 15, wherein the user behavior patterns indicate an infrequently used data set, wherein an infrequently used data set is used less than a predetermined number of times.

* * * * *